United States Patent
Connolly et al.

(10) Patent No.: US 9,806,491 B2
(45) Date of Patent: Oct. 31, 2017

(54) THERMO-ELECTRIC COOLING SYSTEM AND METHOD FOR COOLING ELECTRONIC DEVICES

(71) Applicant: NOVATRANS GROUP SA, Gorgier (CH)

(72) Inventors: John Connolly, Clarksburg, NJ (US); John F. Roulston, Edinburgh (GB); Daniel Mandelik, Rehovot (IL)

(73) Assignee: NOVATRANS GROUP SA, Gorgier (CH)

( * ) Notice: Subject to any disclaimer, the term of this patent is extended or adjusted under 35 U.S.C. 154(b) by 0 days.

(21) Appl. No.: 14/824,964

(22) Filed: Aug. 12, 2015

(65) Prior Publication Data

US 2015/0372448 A1 Dec. 24, 2015

Related U.S. Application Data

(62) Division of application No. 13/520,425, filed as application No. PCT/IL2011/000005 on Jan. 5, 2011, now Pat. No. 9,134,054.

(Continued)

(51) Int. Cl.
*H01S 3/04* (2006.01)
*H01S 3/131* (2006.01)
(Continued)

(52) U.S. Cl.
CPC ............ *H01S 3/1317* (2013.01); *F25B 21/02* (2013.01); *G01N 21/3586* (2013.01);
(Continued)

(58) Field of Classification Search
CPC ....... H04B 7/26; H01S 5/024; H01S 5/02407; H01S 5/02415; H01S 3/0405; H01S 5/12;
(Continued)

(56) References Cited

U.S. PATENT DOCUMENTS

2003/0036303 A1 2/2003 Fang et al.
2005/0045702 A1 3/2005 Freeman et al.
(Continued)

FOREIGN PATENT DOCUMENTS

WO 02/21609 A1 3/2002
WO 2004/053370 A1 6/2004

OTHER PUBLICATIONS

Apr. 30, 2014 Office Action issued in U.S. Appl. No. 13/520,425.
(Continued)

*Primary Examiner* — Yuanda Zhang
(74) *Attorney, Agent, or Firm* — Oliff PLC (57) ABSTRACT

A thermo-electric cooling (TEC) system is presented for cooling of a device, such a laser for example. The TECT system comprises first and second heat pumping assemblies, and a control unit associated at least with said second heat pumping assembly. Each heat pumping assembly has a heat source from which heat is pumped and a heat drain through which pumped heat is dissipated. The at least first and second heat pumping assemblies are arranged in a cascade relationship having at least one thermal interface between the heat source of the second heat pumping assembly and the heat drain of the first heat pumping assembly, the heat source of the first heat pumping assembly being thermally coupled to the electronic device which is to be cooled by evacuating heat therefrom. The control unit is configured and operable to carry out at least one of the following: (i) operating said second heat pumping assembly to provide a desired temperature condition such that temperature of the heat drain of said first heat pumping assembly is either desirably low or by a certain value lower than temperature of the heat source of said first heat pumping assembly; and (ii) operating said second heat pumping assembly to maintain predetermined temperature of said thermal interface.

15 Claims, 6 Drawing Sheets

Related U.S. Application Data (60) Provisional application No. 61/292,649, filed on Jan. 6, 2010.

(51) Int. Cl.
    *F25B 21/02*     (2006.01)
    *H01L 35/32*     (2006.01)
    *G01N 21/3586*     (2014.01)
    *H01S 1/02*     (2006.01)
    *H01S 5/024*     (2006.01)

(52) U.S. Cl.
    CPC .............. *H01L 35/325* (2013.01); *H01S 1/02* (2013.01); *H01S 3/0405* (2013.01); *F25B 2321/021* (2013.01); *H01S 5/02415* (2013.01)

(58) Field of Classification Search
    CPC ...... A63C 1/00; G06Q 10/0639; G06Q 50/01; G06T 11/00
    See application file for complete search history.

(56) References Cited

U.S. PATENT DOCUMENTS

| | | |
|---|---|---|
| 2009/0000652 A1 | 1/2009 | von Windheim et al. |
| 2009/0122493 A1 | 5/2009 | Hosking et al. |
| 2010/0177793 A1 | 7/2010 | Rossi et al. |
| 2010/0277726 A1 | 11/2010 | Logan, Jr. et al. |
| 2012/0326039 A1* | 12/2012 | Demers .................. G01J 3/10 250/338.4 |

OTHER PUBLICATIONS

Jan. 29, 2015 Office Action issued in U.S. Appl. No. 13/520,425.
May 11, 2015 Notice of Allowance issued in U.S. Appl. No. 13/520,425.

* cited by examiner

Fig. 1A (General Art)

Fig. 1B (General Art)

THERMO-ELECTRIC COOLING SYSTEM AND METHOD FOR COOLING ELECTRONIC DEVICES

CROSS-REFERENCE TO THE RELATED APPLICATIONS

This application is a divisional application of U.S. patent application Ser. No. 13/520,425, filed Jul. 3, 2012, which is a U.S. National Stage application claiming the benefit of prior filed International Application No. PCT/IL2011/000005, filed Jan. 5, 2011, in which the International Application claims a priority date of Jan. 6, 2010 based on prior filed U.S. Application No. 61/292,649, the entire contents of which are expressly incorporated by reference herein.

FIELD OF THE INVENTION

This invention relates to a thermo-electric system and method providing for efficient thermoelectric cooling (TEC's) and accurate control of cooling temperature. The invention is highly suitable for implementing fast and accurate control over the output wavelength of Distributed Feedback (DFB) diode lasers.

BACKGROUND OF THE INVENTION

Thermo-Electric Cooling (TEC) devices are generally based on thermo-electric (TE) heat pumps (e.g. solid-state active heat pumps) that use electrical energy to pump and transfer heat from first region(s) of a device to second region(s).

TEC systems are generally characterized by improved pumping performance, such as greater temperature differences obtainable between their "hot" and "cold" regions and higher cooling rates per unit area, in comparison to other cooling techniques. The solid state nature of TEC systems (no moving parts, maintenance-free), as well as their improved pumping performance make them highly suitable for controlling the operation temperatures of many kinds of electronic devices, the proper operation and/or operational properties of which are dependent on their temperature conditions. These include electronic and solid state based devices, as well as optical and electro-optical devices. Also, in certain laser systems maintaining stable temperature it might be essential to stabilize the output frequency of the laser, for which TEC system can be used.

Figure 1A:
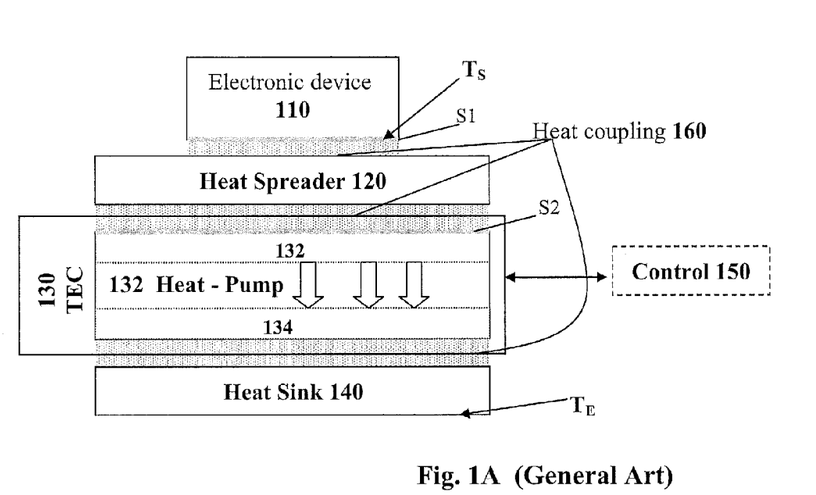
FIGS. 1A and 1B show two examples of the conventional TEC systems.

FIG. 1A illustrates schematically a typical configuration of a TEC system 130 thermally interfacing, through a surface $S_1$ (e.g. being the surface of a heat spreader 120 and/or thermal conductive coupling materials 160), with an electronic device 110 to be cooled, i.e. from which heat should be evacuated. Also, TEC system thermally interfaces through another surface with a heat sink structure 140 for efficient heat exchange with the environment. Utilizing such TEC device for the purposes of heat evacuation from the electronic device 110 (e.g. heat-generating device) enables to maintain/control a working temperature $T_S$ of device 110.

The TEC device should pump heat at a heat rate $dQ_P/dt$ (Qp being the heat pumped by the TEC and t being the time) greater or at least equal to the sum $dQ_S/dt$ ($Q_S$ being the heat generated by the device-to-be cooled) of the heat generation rate of the device 110 and the rate of heat flow from the environment to the device 110 (e.g. due to difference in their temperatures). The achievable heat pumping rate $dQ_P/dt$ of thermo-electric heat pumps typically increases with the dimensions of the surface $S_2$ of the heat pump through which heat is pumped, and decreases with an increase in the temperature difference (against which heat is pumped) between the ambient temperature $T_E$ and the temperature $T_S$ of the device-to-be-cooled 110.

In some cases, for given ambient temperature and operational temperature of the device 110, the heat flux ($dQ_S/dt$) |S1| through the surface(s) $S_1$ of the device 110 is greater than the possible maximal heat flux ($dQ_P/dt$)/ds achievable by thermo-electric heat pump (e.g. through the surface $S_2$). Then, pumping and evacuation of the heat generated by the device 110 can be achieved by utilizing a thermo-electric heat pump 135 having a larger heat pumping surface $S_2$ and a heat spreader 120 for spreading the heat emitted through surface $S_1$ onto the larger heat pumping surface $S_2$.

The amount of heat flux that can be evacuated/pumped from a given surface $S_1$ by utilizing a single thermo-electric heat pump 135 under given ambient conditions (ambient temperature $T_E$) is limited, and accordingly the achievable temperature difference $\Delta T$ between the ambient temperature $T_E$ and the temperature $T_S$ of the device to be cooled is also limited. This is mainly because of the following: as the temperature difference $\Delta T$ increases, an increase in a natural heat flow between hot and cold regions occurs in a direction opposite to the direction of the heat pumping, and the efficiency of heat spreaders at concentrating heat pumping rates (e.g. from a relatively large thermo-electric heat pump (surface $S_2$) to a smaller device (surface $S_1$) from which heat is to be pumped) is also significantly reduced as the ratio of concentration ($S_2/S_1$) increases. Typical temperature difference $\Delta T$ between the cold side (first region) and hot side (second region) of a TEC of this type is limited to about 30-70° C. If larger $\Delta T$ is required, the hot side of one heat pump of the TEC may be cooled using another heat pump in the so-called cascaded configuration of the heat pumps. In such two-pump configuration of the TEC, the achievable $\Delta T$ of the entire TEC is larger (but not twice) than that which might be achieved by a single heat pump.

Known cascaded TEC devices typically include 3 or 4 heat pumps. The cascaded arrangement is typically aimed at providing large $\Delta T$ (e.g. maximal temperature difference) between the hot side and the cold side of the TEC.

Figure 1B:
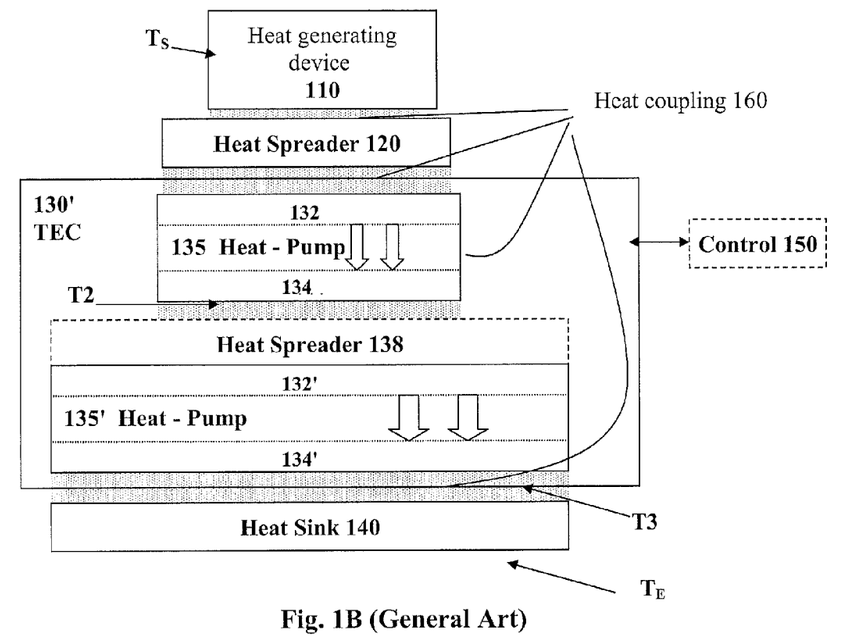

An example of typical TEC device 130' comprising two cascaded heat pumps (e.g. thermo-electric) is illustrated schematically in FIG. 1B. Here, an additional heat pump 135' (e.g. thermo-electric heat pump) is used being thermally coupled in cascade fashion in between the heat pump 135 and heat sink 140 such that the cold side 132' (first region from which heat is transferred) is thermally coupled (e.g. through heat spreader 138) to the hot side 134 (towards which the heat is transferred from cold side) of heat pump 135, and its hot side 134' is coupled to the heat sink 140.

GENERAL DESCRIPTION

There is a need in the art for thermo-electric cooling (TEC) systems capable of fast and accurate control over the operational temperature of a device associated therewith (e.g. being cooled by said TEC).

Many electronic devices require accurate control over their operational temperature. Such electronic devices may be or may include optical devices (e.g. utilizing gratings, frequency multiplier crystals, resonant cavities), as well as other electric or electro-optical devices, such as laser assemblies for which output frequencies might be associated with the operational temperature of the device.

In some cases it is also desirable to provide fast and accurate control over the operational temperature of an electronic device in a manner substantially independent of variable condition(s) such as ambient temperature and/or other external condition which might affect the operational temperature of the device. For example, accurate and fast control over the output wavelength of DFB laser may be achieved via the control of the laser's operational temperature, e.g. by affecting the physical dimensions and thus the optical properties of the device. Such fast and accurate control over a DFB laser output might be of particular importance in creation/emission of Terahertz (THz) radiation. Terahertz emission systems typically utilize photomixing technique of two (or more) DFB lasers having slight difference in their output frequency. The frequency of the output radiation of such photo-mixing process is of the so-called "beat frequency" of the two lasers (being the difference between the frequencies of the DFB lasers). Accordingly, accurate control over the output frequency of at least one of the DFB lasers may provide accurate control over the THz frequency output of the Terahertz emission system. Also, fast control over the output frequency of at least one of the DFB lasers may provide fast frequency modulation over wide band of THz frequency radiation (e.g. between 0.1 THz-4 THz).

Fast and accurate control over the emission of THz radiation is specifically important for various applications such as THz spectroscopy and THz imaging. The invention might be used in THz imaging applications (such as Spectrally-resolved THz imaging and Three dimensional (3D) THz imaging) to enable fast scanning of a sample with multiple THz frequencies in a wide band THz spectrum. High-speed switching between THz frequencies may provide for better performance of the imaging devices and faster results.

Conventionally, controlling the operational temperatures of electronic or electro-optic devices such as a DFB laser (or parts thereof) is achieved in a manner similar to that exemplified in FIGS. 1A and 1B. In the case of DFB lasers (being represented in these figures as a device 110 to be cooled) which typically have higher heat flux density than the TEC 130 can absorb, a heat spreader 120 is used to provide thermo-coupling between the relatively small heat emitting surface $S_1$ of the DFB laser and the larger surface $S_2$ of the TEC 130. Utilizing heat spreader elements is somewhat limited since efficient heat spreading can be obtained only up to a limited heat spreading/concentration ratio ($S_2/S_1$) associated inter-alia with the dimensions of the heat spreader elements and with their specific and absolute heat capacitance. Heat spreaders providing substantially even heat spreading between two surfaces (e.g. $S_2$ and $S_1$) typically have substantially high thermal mass and high heat conductivity.

Alternatively or additionally, cascaded TEC devices (such as 130' of FIG. 1B) are used in order to provide higher capacity/rate of heat pumping from the device 110 (e.g. pumping of greater heat flux through the surface $S_1$) enabling to further increase the temperature difference ($T_E$–$T_S$) between the ambient temperatures $T_E$ and the operating temperature $T_S$ of the device 110 (e.g. further reducing the steady state operating temperature of the device 110 under given ambient temperature $T_E$).

It should be noted that different temperatures referred to in the present disclosure are associated with temperatures measured at certain regions of the TEC device or in its vicinity. Three such temperature measures are disclosed, namely the temperature $T_S$ (relating to or indicative of the device to be cooled), ambient temperature $T_E$ (relating to or indicative of the temperature of the environment), and an interface temperature $T_I$ (described more specifically below). It should be understood that according to the invention, measures indicative of these temperatures might be obtained utilizing various techniques of direct and indirect temperature measurements. Also, the region at which those temperatures are considered/measured may, generally, be constituted by thermal interface regions, such as heat sink or heat spreader at which temperature gradient may exist. In such cases, the respective temperature might be considered at any particular point/region at said thermal interface, or the temperature measure may be a certain function (e.g. average) of the temperatures across the interface.

More specifically, ambient temperature $T_E$ may relate to the temperature of the environment or to the temperature of any region/point of the TEC device, such as any region of a heat sink, through which the TEC is thermally coupled for heat exchange (e.g. dissipation) with the environment. Also, the device temperature $T_S$ may relate to the temperature of the device to be cooled itself or may relate to the temperature at any point/region in the thermal interface (e.g. on a heat spreader) located in between the device to be cooled and a heat pump of the TEC system. Similarly, when referring to a temperature at an interface between certain elements of the TEC (such as an interface between two cascaded heat pumps), a measure indicative of the temperature at any specific, single or multiple, point(s) at said interface might be considered. Moreover, it should be understood that measures of these temperatures (or generally data indicative thereof) may be taken directly, e.g. utilizing thermometers, or indirectly, for example by obtaining indication of the device temperature by analyzing its output (e.g. analyzing its output frequency/wavelength).

Turning back to FIG. 1B, increasing the pumping heat flux through the surface(s) $S_1$ of the device by utilizing the heat spreader 120, the cascaded TEC 130' or both is generally associated with an increase in the effective heat capacity (thermal mass) of the device 110 that is to be cooled. This is because varying the temperature of the device 110 is associated with a change in the temperature of the heat spreader 120. In case of cascaded TEC 130' illustrated in FIG. 1B, varying the temperature of the device 110 may be associated with a change in the temperature of additional elements such as heat pump 135 and heat spreader 138, which typically have significant thermal mass relative to that of the device 110 itself.

TEC devices/systems are typically used to cool elements to a certain constant temperature and not for fast tuning of the temperature. Accordingly, typically, cascaded TEC devices/systems are not used for increasing the speed of the cooling system (temperature change in time). One of the primary difficulties with the conventional methods for increasing the pumping heat flux from the device being cooled, is related to a decrease in the speed of a response (temperature change) of the device 110. This is due to the increase in effective heat mass that is to be cooled together with the device 110. Hence, according to the conventional methods, thermal response time of the system (i.e. the time scale for temperature variation, e.g. the ability to change the temperature of the DFB laser and supporting material in a short time) is limited. This is because configuring known heat pumps (e.g. thermo-electric) such as to provide an increase in the heat pumping rate through a surface of a given size (increasing the pumping heat flux in order to reduce the time scale for temperature change) is generally accompanied with an increase in the effective thermal mass that is to be cooled (e.g. due to the presence of heat spreader). The total thermal mass that is to be cooled, in this case, is associated with the thermal mass of the device 110 itself and with effective thermal mass of some elements such as the heat spreader and the TEC 130/130'. The minimal thermal response time is therefore determined by a fine balance between the effective thermal mass of the system (which is greatly affected, for instance, by the presence of a heat spreader) and the obtainable pumping heat flux.

The inventors of the present invention have realized that the heat pumping rate of thermo-electric heat pumps substantially improves with the increase of the temperature of a heat source of the heat pump (i.e. a side/interface of the pump from which heat is pumped and with which the device to be cooled is thermally coupled) and with the decrease in the temperature of a heat drain of the pump (i.e. a side/interface of the pump from which heat is dissipated). Hence, by maintaining any one of such conditions, as a relatively low temperature of the heat drain of the pump and a relatively high temperature at the heat source of the pump, the heat pumping rate can be substantially increased. Preferably, a negative temperature difference is maintained between the heat drain and the heat source of the pump. Cooling the heat drain of a heat pump enables to provide superior cooling rates with respect to a device attached to the heat source of the pump. Equivalently, heating the heat source of the pump enables to provide superior heating rates with respect to a device attached to the heat drain.

The inventors of the present invention have understood that such high heat pumping efficiency/heat pumping rate (enabling to provide fast cooling) can be obtained by appropriately arranging at least two heat pumping assemblies in a cascade (i.e. each being formed by a single heat pump or by multiple heat pumps, e.g. in cascade arrangement). The arrangement of at least two heat pumping assemblies is such that a heat source of the first pumping assembly (referred to as a "first pump") is associated with the device to be cooled and is configured for pumping heat therefrom, and the heat source of the second pumping assembly (referred to as "second pump") thermally interfaces (i.e. is arranged for enabling heat exchange with) the heat drain of the first pump and operates to maintain low and preferably negative temperature difference between the heat drain and the heat source of said first pump.

Another factor which affects the response time is the maximal temperature difference ($\Delta T = T_E - T_S$) that can be achieved between the hot and cold sides of the TEC (heat source and heat drain sides). This limit occurs because the natural heat flow occurs from the hot to the cold side within the TEC system. The natural heat flow increases with the temperature difference, whereas the heat pumping rate of the TEC system is more or less independent of this temperature difference. Hence, there exists a temperature point where the net heat flow becomes zero and the TEC system is no longer effective. The maximal temperature difference $\Delta T$ is typically between 30° C. and 70° C.

In general, the lower is the temperature of the heat drain of the heat pump relative to its heat source, the higher is the heat pumping rate of the TEC system. For a negative temperature difference $\Delta T$ between the heat drain and heat source (the nominal "cold" side is warmer than the "hot" side), the heat pumping rate is even higher (than a positive temperature difference $\Delta T$), since the thermal pumping and the natural heat flow occur in the same direction.

Hence, in accordance with the present invention, the second heat pump is configured and operated for obtaining a low/negative temperature difference between the heat drain and heat source of the first pump. This may for example be achieved by configuring the second heat pump for pumping heat from the heat drain of the first pump with heat pumping rate greater than the rate of heat provision (by the device being cooled) at the heat source side of the first pump. Accordingly, a control unit might be provided being configured and operable to control the rate of heat pumping of the second heat pump in order to provide the desirable temperature difference (e.g. within a certain range) between the heat drain and source of the first pump, or alternatively to maintain a certain fixed temperature (or a certain fixed range) of the heat drain of the first pump which is substantially low relative to the average temperature of the heat source of the first pump.

The following description of the invention focuses mainly on a cooling system, namely a system configured for cooling a device (also sometimes referred to herein as a device-to-be-cooled). It should however be understood that the principles of the invention can also be utilized for heating or for carrying out both the cooling and heating of a device with superior heat pumping (cooling/heating) rates. As noted above, cooling the heat drain and/or heating the heat source of a TE heat pump provides greater heat pumping rates. The functionality of heating is achieved by operating first and second heat pumps in a similar manner as described below for cooling the device but only with a heat pumping direction opposite to that required for cooling.

Enabling both the superior cooling and the superior heating of a device might be achieved according to the invention by utilizing a cascaded TEC system incorporating at least first and second, bi-directional (reversible) heat pumps, arranged in a cascade fashion such that the first heat pump intermediates between the device and the second pump. It should be noted that for brevity, the region of the first heat pump to which the device is attached (generally, with which the device interfaces) and from which heat is pumped during cooling of the device is referred to herein as the heat source of the first pump, and regions towards which heat is transferred are referred to as heat drain. However, during heating of the device, when the operation of the first and second heat pumps is reversed, the same regions actually function as respectively heat drain and heat source.

A TEC system according to the invention, capable of both cooling and heating an electronic device, can be advantageously used in DFB laser systems in which the output wavelength depends on the temperature of the laser. The use of the TEC system capable of both cooling and heating of the laser with superior heat pumping rates enables fast tuning of the laser within a relatively wide spectral range.

The first pump is operated to control the temperature of the device to be cooled by pumping heat therefrom. The invention enables fine temperature tuning and rapid temperature changes to be obtained in the device to be cooled. This is achieved according to the invention by at least one of the following: (1) increasing the achievable heat pumping rate by maintaining a negative temperature difference between the heat drain and source of the first heat pump as noted above; and (2) reducing the "effective heat capacity" (effective thermal mass) of the device to be cooled which is defined by the measure of the heat energy that needs to be pumped (e.g. by the first pump) in order to reduce the temperature of the device to be cooled by a certain temperature interval.

The effective heat capacity of the device to be cooled is associated with the heat capacity of the device itself, and with a certain effective heat capacity associated with the heat capacities of some of the elements of the heat pumping assembly (such as thermo-electric heat pumps, heat spreader/sink), and also with the variations of the temperature of these elements that occur while the temperature of the device to be cooled is changed. To this end, minimizing the heat capacity of those elements the temperature of which significantly changes with a change in the temperature of the device-to-be-cooled and/or minimizing the number of such elements, enables to reduce the effective heat capacity of the device to be cooled and thus to further reduce the characteristic time scale associated with a change in the temperature of the device (reducing the thermal response time of the system).

This is achieved, according to the invention, by configuring the TEC system as having at least two heat pumping assemblies (i.e. each being formed by an arrangement of one or more heat pumps) which are arranged in a cascade as noted above. The first heat pumping assembly thermally interfaces the device to be cooled by its heat source for pumping heat therefrom and has a thermal interface, at its heat drain, with the heat source of the second pumping assembly. Preferably, in order to minimize the effective heat capacity of the device to be cooled, the first pumping assembly (including all the elements located in between said thermal interface (heat source of the first pump) and the device to be cooled) is configured for having minimal heat capacity, while the second pumping assembly (which might have arbitrary heat capacity) is configured and operable to maintain the thermal interface (the heat drain of the first pump and the heat source of the second pump) at substantially constant temperature irrespective of the temperature or temperature variation (fine tuning) that is to be obtained at the device-to-be-cooled. This arrangement provides for reducing the effective thermal mass of the device to be cooled and further reducing the thermal response time. This is because the only elements of the heat pumping assembly whose temperature substantially varies with the variation of the temperature of the device are the elements of the first pumping assembly configured for having minimal thermal mass.

It should be noted that according to the invention, the second pumping assembly may be operated by the control unit to maintain the thermal interface between the first and second heat pumping assemblies. This can be performed by maintaining the thermal interface at substantially constant temperature, or by maintaining the temperature of the thermal interface at substantially constant temperature interval with respect to the temperatures of any one of the heat source of the first pumping assembly and/or the ambient temperature at the heat drain of the second heat pumping assembly. Such arrangement enables the control unit to operate the first pumping assembly (which implements cooling of the device) with a relative certainty regarding the temperature condition of the thermal interface to which heat is drained by the first pump, thus enabling to provide further accurate tuning over the temperature of the device to be cooled.

Alternatively, the second pumping assembly may be operated by the control unit to maintain the thermal interface between the first and second heat pumping assemblies at the lowest achievable temperature to enable fast temperature changes in the device. This might be achieved by a continuous operation of the second heat pumping assembly regardless of the temperature at said interface. Additionally, in such a case, the use of either a thermometer at the interface and/or the use of a control unit for controlling the operation of the second heat pumping assembly may be obviated.

In accordance with the above considerations, typically a thermo-electric heat pump is utilized as the first pumping assembly in order to provide substantial heat pump density of about 50-100 mW/mm$^2$ and relatively low heat mass and thus relatively high ratio between the heat pumping rate and the thermal mass of the first heat pump which enables superior thermal response time of the system. Preferably, the first heat pump assembly utilizes thermo-electric heat pump device(s) based on thin-film technology (such as available from Micropelt Company, Germany). Such devices provide improved heat pump densities, e.g. of about 300-1000 mW/mm$^2$, and by utilizing such a device the ratio between the heat pumping rate and the thermal mass is further increased and the thermal response time and characteristic cooling time scale of the cooling system is further decreased, enabling faster temperature variations of the device to be cooled.

It should be noted that according to the invention the control unit utilizes at least one sensing unit (e.g. temperature sensor/thermometer) that provides indication relating to the temperature of the device to be cooled (and/or the temperature of the heat source of the first pumping assembly). The sensing unit is not necessarily a thermometer but may be based on other parameters which are indicative of the temperature. For example, in case the device to be cooled is a DFB laser, measurements of the laser's output wavelength may provide indication to its temperature. For clarity, the term temperature sensor is used herein to indicate any sensing unit that is suitable for providing indication relating to the respective temperature that is to be measured/determined.

The control unit typically operates the first pumping assembly in accordance with the read out from this temperature sensor (e.g. thermometer) and in accordance with the desired temperature of the device-to-be-cooled. The control unit may generally utilize at least one additional temperature sensor (e.g. thermometer) to measure the temperature of the thermal interface between the first and second heat pumping assemblies and to operate the second pumping assembly in accordance with the read out of said additional thermometer in order to control the desired temperature of the interface.

It should be understood that the interface between the first and second pumping assemblies might be defined as a region at which the temperature is measured by said additional temperature sensor and in which the temperature is maintained by the operation of the second heat pumping assembly. In many cases, a heat spreader or other heat coupling device(s) is/are accommodated at the thermal interface between the first and second heat pumping assemblies. Typically, the heat spreader has substantial thermal mass which may, as explained above, impair and reduce the thermal response time of the TEC system. Hence, in order to avoid consequent decrease in the thermal response time of the TEC system of the present invention, the thermal interface, between the first and second pumping assemblies, at which the temperature is measured (by said thermometer) and maintained by the second pumping assembly, is preferably located between the heat spreader and the heat drain of the first heat pumping assembly. In other words, typically such heat coupling element, as a heat spreader, which is located in between the first and second heat pumping assemblies and which have substantial heat capacity, is considered as a part of the second heat pumping assembly, and the temperature at the interface is measured at the region between this heat coupling element and the first pumping assembly. Thus, thermal mass of the first pumping assembly and the effective thermal mass of the device to be cooled (e.g. which is associated also with the thermal mass of the first pumping assembly) are maintained substantially low regardless of the thermal mass of such heat coupling element.

Thus, according to one broad aspect of the invention, there is provided a thermo-electric cooling (TEC) system for cooling of a device, the TEC system comprising:

at least first and second heat pumping assemblies, each heat pumping assembly having a heat source from which heat is pumped and a heat drain through which pumped heat is dissipated, said at least first and second heat pumping assemblies being arranged in a cascade relationship having at least one thermal interface between the heat source of the second heat pumping assembly and the heat drain of the first heat pumping assembly, the heat source of the first heat pumping assembly being thermally coupled to an electronic device which is to be cooled by evacuating heat therefrom; and a control unit associated at least with said second heat pumping assembly, and configured and operable to carry out at least one of the following: (i) operating said second heat pumping assembly to provide a desired temperature condition such that temperature of the heat drain of said first heat pumping assembly is either desirably low or by a certain value lower than temperature of the heat source of said first heat pumping assembly; and (ii) operating said second heat pumping assembly to maintain predetermined temperature of said thermal interface.

The second heat pumping assembly may comprise one or more thermo-electric heat pumps. Similarly, the first heat pumping assembly may comprise one or more thermo-electric heat pumps, e.g. based on the thin film technology. The first and/or second heat pumping assemblies may include more than one heat pump, which are arranged in a cascade fashion.

In some embodiments of the invention, the control unit is configured and operable to operate the second heat pumping assembly to provide the temperature of the heat drain of the first heat pumping assembly lower than the temperature of the heat source of the first heat pumping assembly.

In some embodiments of the invention, the control unit is configured and operable to operate the second heat pumping assembly to maintain predetermined temperature of the thermal interface. The predetermined temperature may be a certain constant temperature value; or a relative value corresponding to a substantially constant temperature difference between the thermal interface and any one of ambient temperature and the temperature of the device being cooled.

In some embodiments of the invention, the control unit is configured and operable to controllably operate the first heat pumping assembly in order to control the temperature of the device.

The control unit may be configured and operable for operating the second heat pumping assembly to maintain substantially constant temperature of the thermal interface, and for generating an operation scheme specifying the heat pumping rates and respective durations according to which the first heat pumping assembly is operated in order to accurately adjust the temperature of said device. The operation scheme may be generated based on at least one of the following parameters: the current and desired temperatures of the device, the effective thermal mass of said device, the temperature of said thermal interface and the thermal conductivity of said device.

According to another broad aspect of the invention, there is provided a thermo-electric (TE) system for controlling operation of a THz emitter which comprises first and second lasers, the TE system comprising: the above-described TEC system for controlling the temperature condition of the first laser; and an additional TEC system comprising two heat pumping assemblies, each having a heat source from which heat is pumped and a heat drain through which pumped heat is dissipated, the heat pumping assemblies of the additional TEC system being arranged in a cascade relationship having at least one thermal interface between the heat source of one of the heat pumping assemblies and the heat drain of the other heat pumping assembly, the heat source of said one of the heat pumping assemblies being thermally coupled to the second laser which is to be heated by transferring heat thereto.

The same control unit may be used for operating the additional TEC system to carry out the following: operating its second heat pumping assembly to provide a desired temperature condition such that temperature of the heat drain of said first heat pumping assembly of the additional TEC system is either desirably high or by a certain value higher than temperature of the heat source of said first heat pumping assembly.

According to yet further aspect of the invention, there is provided a thermo-electric cooling (TEC) system for cooling an electronic device, the TEC system comprising at least first and second heat pumping assemblies, each of the heat pumping assemblies having a heat source from which heat is pumped and a heat drain through which pumped heat is dissipated, said at least first and second heat pumping assemblies being arranged in a cascade relationship having at least one thermal interface between the heat source of the second heat pumping assembly and the heat drain of the first heat pumping assembly, the heat source of the first heat pumping assembly being thermally coupled to an electronic device which is to be cooled by evacuating heat therefrom, said second heat pumping assembly having a substantially larger heat pumping rate than the first pumping assembly, such that when the TEC system is in operation a negative temperature difference is obtained between the heat drain and the heat source of the first heat pumping assembly.

The invention in its yet another aspect provides a control system for controlling thermo-electric cooling of an electronic device, said control system being connectable to one or more temperature sensors and to a cascaded TEC system, which comprises first and second heat pumping assemblies, where the first heat pumping assembly is thermally coupled with the device by a heat source of the first heat pumping assembly, and is serially coupled to a second heat pumping assembly through a thermal interface in between a heat source of the second heat pumping assembly and a heat drain of the first heat pumping assembly, the control unit being configured and operable for selectively carrying out at least one of the following to implement substantially fast and accurate tuning of the temperature of the electronic device:

obtaining from at least one of the temperature sensors data indicative of temperature at the thermal interface between the first and second heat pumping assemblies, analyzing said data, and controlling operation of the second heat pumping assembly in order to maintain a predetermined temperature condition of said thermal interface, said predetermined temperature condition including at least one of the following: a substantially constant temperature value, a desirably low temperature value;

obtaining from at least one of the temperature sensors data indicative of temperature of the device to be cooled; analyzing said data, and controlling the operation of the first heat pumping assembly in order to maintain desired temperature of said device.

According to a further broad aspect of the invention, there is provided a laser system having at least a first laser source; and a thermo-electric (TE) system configured and operable for cooling and/or heating of said at least first laser source according to a predetermined temperature sweeping scheme thereby providing fast sweeping of a frequency output of the laser system.

BRIEF DESCRIPTION OF THE DRAWINGS

In order to understand the invention and to see how it may be carried out in practice, some embodiments will now be described, by way of non-limiting example only, with reference to the accompanying drawings, in which:

FIGS. 4A to 4C show a specific example of the TEC system of the invention for cooling a DFB laser device, where

DETAILED DESCRIPTION OF EMBODIMENTS

FIGS. 1A and 1B exemplify TEC systems configured according to the conventional approach. FIG. 1A shows the TEC system using a single heat pump, and FIG. 1B shows the TEC system using a cascade of two heat pumps.

Figure 2A:
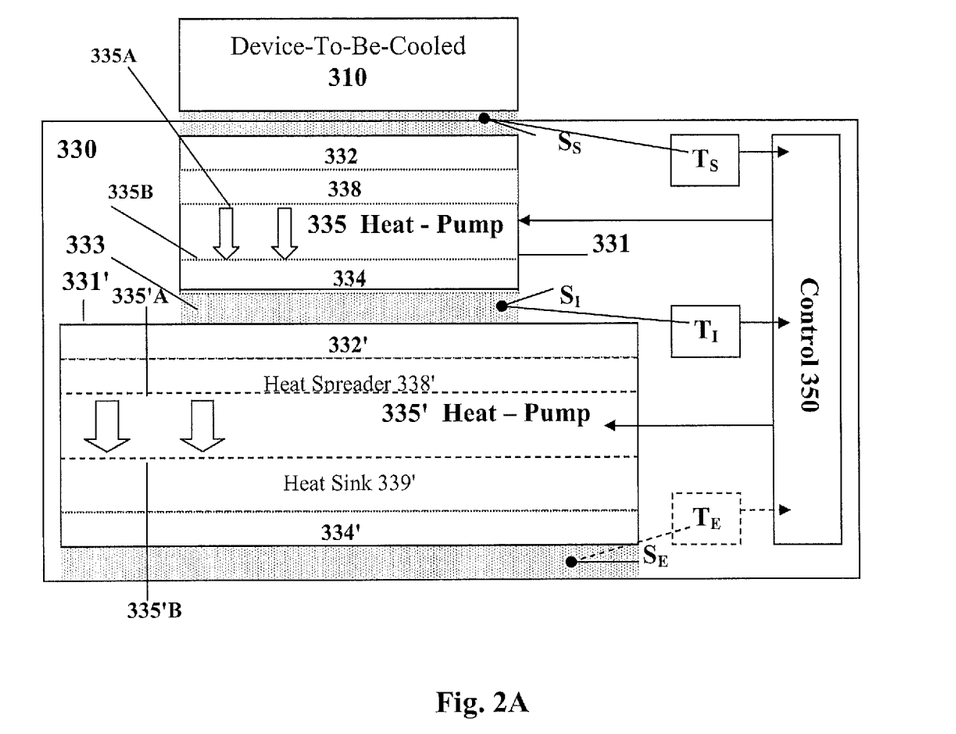
FIG. 2A illustrates a block diagram of an example of a TEC system of the present invention.

Reference is made to FIG. 2A illustrating schematically a Thermo-Electric Cooling (TEC) system 330 according to an embodiment of the present invention. The TEC system 330 is associated with (thermally coupled to) an electronic device 310 constituting a device-to-be-cooled. According to this embodiment, TEC system 330 includes first and second heat pumping assemblies 331 and 331' associated with a control unit 350 (i.e. are connectable to the control unit via wires or wireless signal transmission).

Each of the heat pumping assemblies 331 and 331' has a heat source (332 and 332' respectively) from which heat is pumped by the pumping assembly, and a heat drain (334, 334' respectively) to which the pumped heat is transferred and/or dissipated by the pumping assembly. Heat pumping assemblies 331 and 331' are arranged in a cascade relationship with respect to one another such that the second heat pumping assembly 331' operates to pump heat from the heat drain 334 of the first heat pumping assembly 331. To this end, the heat source 332' of the second heat pumping assembly 331' thermally interfaces (e.g. is coupled to) the heat drain 334 of the first pumping assembly 331 through a thermal interface 333 which is preferably of a high thermal conductivity. According to the invention, each of the heat pumping assemblies 331 and 331' includes one or more heat pumps which may be arranged in any suitable fashion (e.g. in cascade). The heat pumping assemblies may also include various heat transfer and dissipation elements/mechanisms, such as heat spreaders, heat dissipaters (heat sinks) and heat conductive elements, interfacing and thermally coupling between the various elements of the pumping assemblies.

In the embodiment of FIG. 2A, the first pumping assembly 331 includes a single thermo-electric heat pump 335 configured for pumping/transferring heat from one of its facets 335A to another facet 335B of the pump 335. Facet 335A of the heat pump 335 from which the heat is pumped may by itself serve as the heat source 332 of the assembly 335. Alternatively, as exemplified in the figure, facet 335A may optionally be coupled with one side of a heat spreader/concentrator 338 whose other side serves as the heat source 332 of the assembly 331. In this embodiment, also the second heat pumping assembly 331' includes a single heat pump 335' (e.g. thermo-electric) configured for pumping/transferring heat from one of its facets 335'A to another facet 335'B. Similarly, facet 335'A of the heat pump 335' (from which heat is pumped) may by itself serve as the heat source 332' of the assembly 335', or, as exemplified in the figure, it may optionally be coupled to a heat spreader/concentrator 338' that serves as the heat source 332' of the assembly 335'. Also, facet 335'A of the heat pump 335' may by itself serve as the heat drain 334' of the assembly 331' or, it may be coupled with a heat sink 339' serving as the heat drain 334'.

The control unit 350 is configured and operative for controlling the operation of the heat pumping assemblies 331 and 331' in accordance with the temperature of the device 310 to be cooled, and optionally also in accordance with a temperature profile across the TEC system. To this end, the control unit 350 is typically associated (connectable to) one or more sensing units ($S_1$, $S_S$) (also referred to as temperature sensors, e.g. thermometers) configured for providing data indicative of the temperatures $T_I$, $T_S$ of the device 310 and of the interface 333 respectively.

The control unit 350 is configured for controlling the heat pumping rate of each of the pumping assemblies 331 and 331' for providing the desired temperature accuracy and/or desired temperature change rates in the temperature of the device 310. To this end, the control unit is operable in one of the two modes or both of them to respectively maintain at least one of the following conditions: It can maintain the temperature of the interface 333 at a fixed value, substantially independently from the momentary temperatures of the environment (ambient temperatures) and/or the device 310 to thereby enable accurate control over the device's temperature.

It should be understood that the control unit 350 might be implemented as a single unit controlling the TEC's operation or implemented utilizing multiple controllers/processors (not shown) which may operate independently, or not, from each other. For example, in case two controllers are used, a first controller may be associated with the operation of the first heat pumping assembly 331 for controlling the temperature of the device 310 and the second controller associated with the operation of the second heat pumping assembly 331' for controlling the temperature of the interface 333.

The device 310 to be cooled may be any device, e.g. electronic device such as laser, e.g. DFB laser. As indicated above, the invention can advantageously be used in THz emitter systems. Such systems may utilize a pair of lasers with slightly different operational wavelengths to cause THz-range beat frequency pulses. In such systems, fine tuning of the operational temperature and thus operational wavelength of at least one or both lasers is very important to define the emitting frequency, and also for many applications the ability of the system to be fast tunable is an important property. In such systems, the invented cooling system may be a two-part system, the two parts being associated with the two lasers respectively. One of the parts of the system would be configured and operable as a cooler configured as described above for cooling its associated laser, while the other system would be configured generally similar and operable as a heater, i.e. in the opposite manner (the functions of the heat source and drain would be interchanged) for implementing heating of the respective laser. Shifting the output THz frequency across a required range can be achieved by heating and cooling of the respective lasers in an alternating fashion. The same control unit can be used for appropriately operating the cooler and heater parts of the TEC system.

Figure 2B:
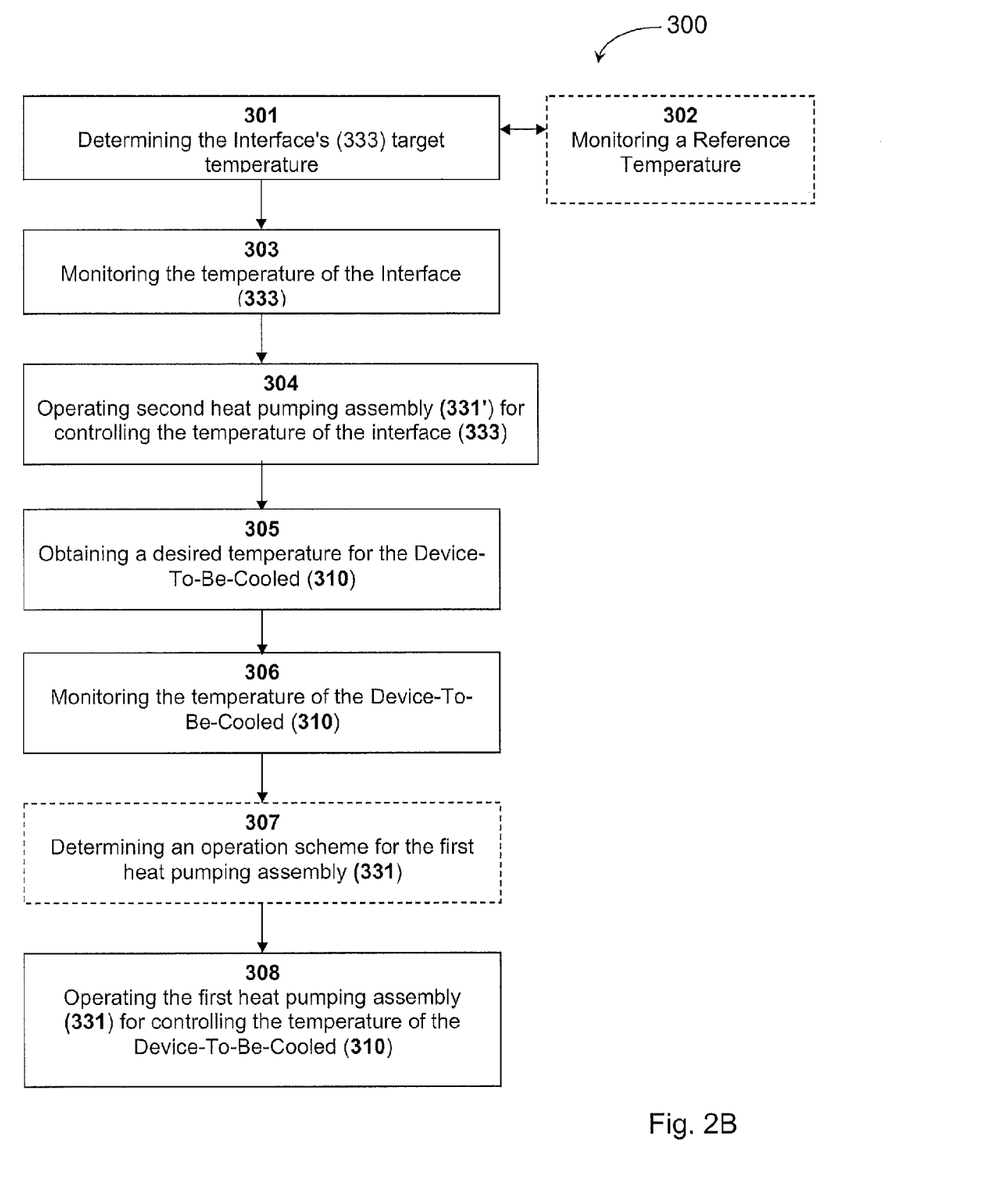
FIG. 2B illustrates a flow diagram of a method according to an embodiment of the invention.

Turning now to FIG. 2B, there is illustrated a flow chart 300 of a method of the present invention (that can be carried out by the control unit) for controlling the temperature of the device to be cooled. For clarity and without loss of generality, when referring to elements of the TEC system of the invention, reference numerals of FIG. 2A are used. Steps 301-304 of the method are associated with the operation of the control unit aimed at adjusting and controlling the temperature of the interface 333. As noted above, low temperature of the interface 333 enables to rapidly change the temperature of the device 310, while accurate adjustment of the temperature of the interface 333 enables fine control over the temperature of the device 310.

A target temperature of the interface is dependent on the desired operational mode of the TEC system. Generally, the control unit 350 operates to maintain one or more of the following modes (conditions) by properly controlling the operation of the second heat pumping assembly 331'.

(i) In a first mode of operation, the target temperature of the interface (333) is defined as a low temperature, preferably the lowest that can be achieved by proper operation of the second pumping assembly 331' to allow the highest rates of temperature changes in the device 310. The value of such target temperature might not be specifically designated. The control unit can operate the second pumping assembly 331' to maintain the temperature of the interface 333 at a low value, which is preferably below the average temperature (nominal temperature) of the device 310 during its operation. This enables high heat pumping rates to be achieved by the first pumping assembly 331 and to thereby enable fast changes of the temperature of the device 310.

(ii) In a second mode of operation, the target temperature of the interface (333) is defined as a certain fixed temperature (preferably lower than the device's 310 nominal temperature) which is independent of other variables of the system/environment to thereby enable accurate and fine tuning of the device's temperature.

(iii) In a third mode of operation, the target temperature of the interface (333) is defined at a certain interval from a certain reference temperature (e.g. which might be the temperature of the device 310 or the temperature of the environment optionally monitored in step 302 below).

The method described hereafter might be carried out by the control unit for monitoring and controlling the temperature of the interface in accordance with the above modes.

In step 301, a target temperature of the interface 333 is determined in accordance with the desired operational mode of the TEC system. Optional step 302, in which a certain reference temperature is monitored, is carried out when the target temperature of the interface is determined in accordance with said certain reference temperature.

In step 303, the control unit operates to monitor a temperature $T_I$ at the interface 333 between the first and second pumping assemblies 331 and 331'.

In step 304, the temperature of the interface 333 is maintained about said target temperature (within a certain predetermined temperature range). Upon detecting that temperature $T_I$ exceeds the target temperature value (which is to be maintained) by a certain predetermined threshold, the control unit operates the second pumping assembly 331' to pump heat from said interface 333 and to thereby reduce and maintain its temperature at said target value.

It should be noted that steps 302 to 304 might be obviated in case that the target temperature $T_I$ of the interface is determined (in step 301) as the lowest achievable temperature. In these cases, the second heat pumping assembly might be operated continuously for reducing the interfaces' temperature to the lowest possible value (e.g. without monitoring the interface temperature).

The control unit also operates to control the temperature of the device to be cooled 310 in accordance with a desired temperature at which the device 310 is to be operated. The temperature of the device is generally controlled by the operation of the first heat pumping assembly 331. In step 305, the desired operational temperature of the device 310 is obtained (e.g. from external data source or user interface). The temperature ($T_S$) of the device 310 is monitored (step 306).

The measurements (monitoring) of the temperature $T_S$ of the device and the temperature $T_I$ at the interface 333 also enable to use the measured temperature difference ($T_I$-$T_S$) and provide an accurate estimation of the heat pumping rate of the first heat pumping assembly 331 and thus provide improved tuning accuracy in the variations in the device temperature $T_S$. Optionally, when fine and accurate adjustment of the device's 310 temperature is desirable, an operation scheme, specifying the intensity(ies) (heat pumping rates) and duration(s) of operation of the first heat pumping assembly, is determined (step 307). Such operation scheme is determined in accordance with at least some of the following parameters: temperature difference between the monitored ($T_S$) and desirable temperatures of the device 310; the effective heat capacity of the device; the heat conductance through the device; the temperature $T_I$ of the interface 333.

Such operation scheme for operating the first heat pumping assembly 331 enables optimal (i.e. both accurate and fast) temperature changes in the device and minimizes the correction and delays that might be caused by over- and/or under-cooling of the device.

Finally, in step 308 the operation of the first pumping assembly 331 is controlled in accordance with the measured temperature $T_S$ of the device 310 and optionally also in accordance with the temperature $T_I$ of the interface 333 and with the operation scheme to enable fast and/or accurate temperature maintenance/change.

Turning back to FIG. 2A, in order to enable fast temperature changes of the device to be cooled 310, the first heat pumping assembly 331 is configured with relatively low heat capacitance and high pumping rate, lower than those of the second pumping assembly 331'. This might be achieved for example by utilizing a thin-film TEC as the first heat pumping assembly 331. Such a thin-film TEC is known as a Micro-Peltier cooler which has a heat pump rate of about 600 mW/mm². Alternatively, the same effect can be achieved by configuring the interface 333 in between the heat pumping assemblies 331 and 331' (defined as the region at which the temperature $T_I$ is measured) to eliminate the use of heat coupling elements (associated with the interface) in the first pumping assembly 331 and optionally include such elements in the second assembly 331' outside the region between the interface 333 and the device 310), to thereby reduce the heat capacity of the first heat pumping assembly 331. Eliminating the use of heat coupling elements, such as heat spreader, in the first heat pumping assembly 331 may provide substantial reduction in the thermal mass of the first heat pumping assembly 331 and accordingly reduce the effective thermal mass of the device to be cooled. It should be noted that heat spreaders, which are configured for efficient spreading of heat flux, typically have substantial thermal mass.

According to the conventional approach, efficient heat spreaders are used to effectively transfer heat from the electronic device (e.g. DFB laser) to the TEC system or in between the heat pumping assemblies of the TEC system. For example the heat flux density of a typical DFB laser chip (e.g. a 1 mm long, p-mounted chip operating at 200 mA) may be 10-50 times higher than the heat flux density pumped by a conventional TEC system. However, using an efficient heat spreader (capable of spreading the heat flux over an area of 10-50 times greater might impair the time scales associated with variation of the temperature of the DFB laser. This is because the heat spreader typically adds significant thermal mass, thus increasing the effective thermal mass of the electronic device. However, higher thermal mass constrains the ability to shift the system temperature rapidly and increases the time scale for cooling the electronic device. Accordingly, the control unit operates to stabilize the temperature.

The invention enables to use heat coupling elements of lower thermal mass in between the device and the first pumping assembly. This is because the heat pumping rate (per unit area) of the first heat pumping assembly and the density of the heat flux pumped from the electronic device is improved (e.g. due to the low and preferably negative temperature difference between the heat drain and heat source of the first heat pumping assembly). Hence, in addition to a low cooling time scales obtained due to the improvement in the pumping heat flux, the cooling time scale of the system is further reduced due to lowering the effective thermal mass of the device.

It should be noted that according to the conventional approach for the cascade TEC system, a first heat pump serves to pump heat at a certain rate from the device to be cooled, and a second heat pump operates at a heat pumping rate of the same order of said certain rate to enable improved heat dissipation of the heat from the heat drain of the first pump. Conversely, according to the present invention, substantially faster cooling rates can be achieved owing to the provision of a relatively low temperature at the interface between the first and second heat pumps, e.g. the second heat pump is operated to simulate low ambient temperatures for the first heat pump (the second heat pumping assembly 331' is capable of heat pumping rates substantially higher than that of the first heat pumping assembly 331).

Figure 3:
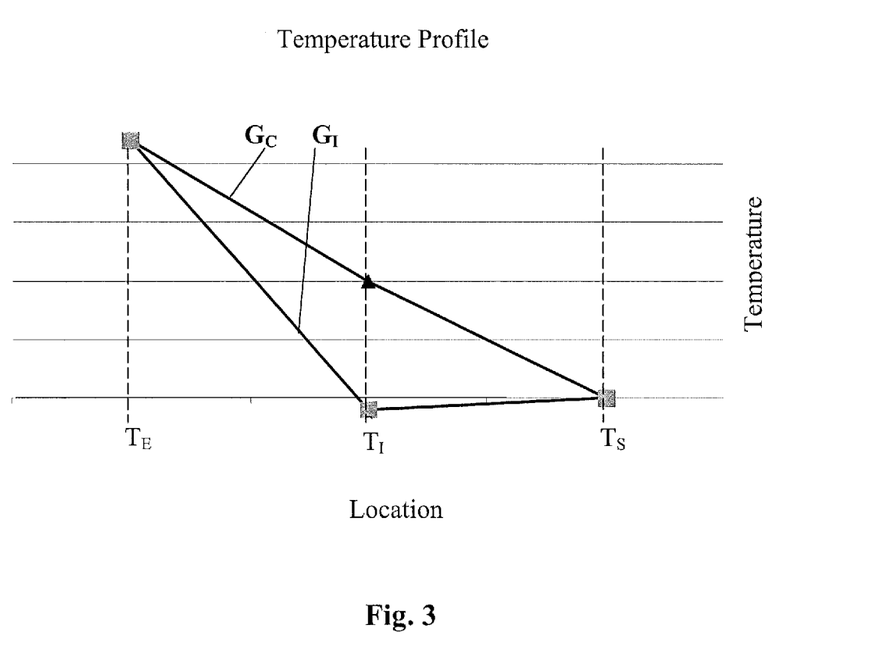
FIG. 3 graphically compares the temperature profiles through the conventional TEC and the TEC system of the invention.

Reference is now made to FIG. 3 which illustrates schematically (in arbitrary temperature units) comparison between temperature profiles $G_C$ and $G_I$ of two cascaded TEC systems configured according to the conventional technique and according to the invention, respectively. The temperature profiles represent the obtainable temperatures at three regions of the cascaded systems, namely: (1) $T_S$—at the interface between the device to be cooled (310 in FIG. 2A) and the first pumping assembly 331; (2) $T_I$—at the interface 333 between the first and second pumping assemblies 331 and 331', and (3) $T_E$—the ambient temperature (e.g. at the interface between the second pumping assembly and the surroundings). For simplicity, the temperature profiles in both cases correspond to a condition that the devices to be cooled are not generating any heat (are inoperative), and thus the cooling operation acts only to cool the device and to counteract natural heat flow from the surroundings to the device due to the temperature differences. Moreover, similar ambient temperatures and cooling rates are considered. As shown in the figure, according to the invention, the temperature $T_I$ is controllably maintained at very low values, preferably below the temperature of the device to be cooled (e.g. below $T_S$), while according to the conventional technique the temperature $T_I$ of the interface 333 is naturally obtained within the range between the ambient temperature $T_E$ and the device temperature $T_S$.

Also, conversely to the existing approach according to which the temperature at the interface between two cascaded heat pumps is not controlled, the inventions provides for controlling this temperature. This control is aimed at and enables to obtain negative temperature difference ΔT between the sides of the first heat pumping assembly, which are coupled with the second heat pumping assembly and with the device to be cooled, receptively, and alternatively or additionally, enables to provide stabilization of the temperature at the interface (333 in FIG. 2) between the pumping assemblies 331 and 331' to enable accurate control over the temperature of the device to be cooled.

As noted above, the invention is adapted for rapidly changing the temperature of the electronic device, such as DFB laser, with fine accuracy, thereby enabling accurate and fast variations of the lasers output (wavelength/frequency). A specific but not limiting example of the configuration of DFB laser with the TEC system of the present invention is illustrated by way of a block diagram in FIG. 4A. The entire DFB assembly is shown, in a self-explanatory manner, in FIGS. 4B and 4C. For clarity, reference is made to these figures together and the same reference numerals are used to designate common elements shown.

Figure 4A:
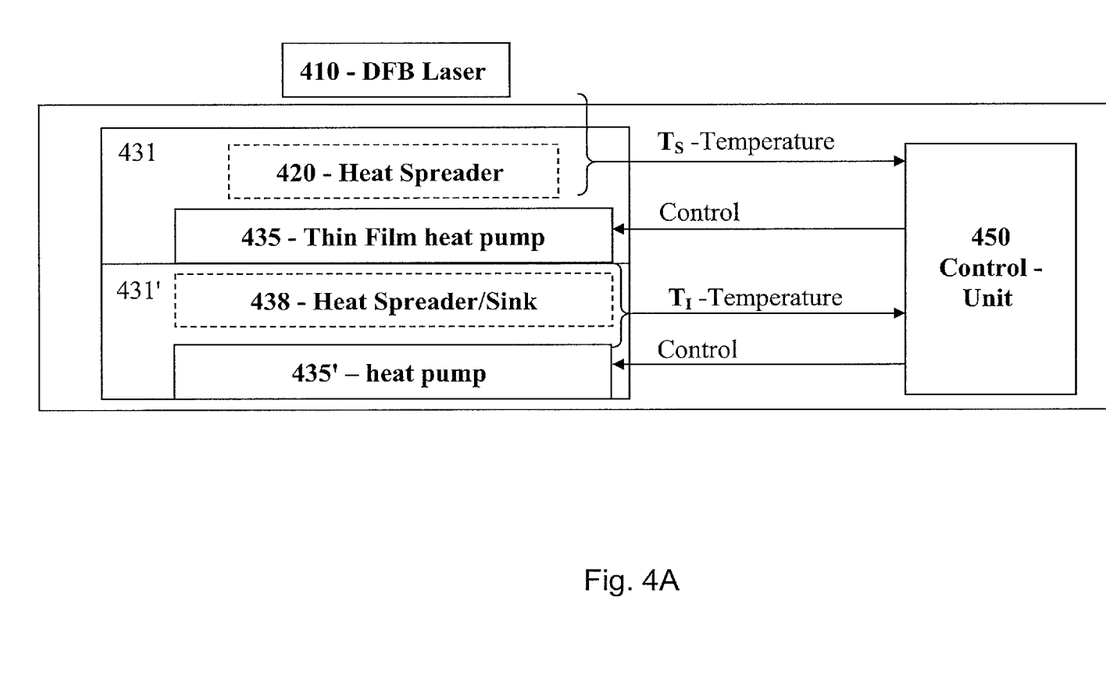
FIG. 4A shows a block diagram of the TEC system.
Figure 4B:
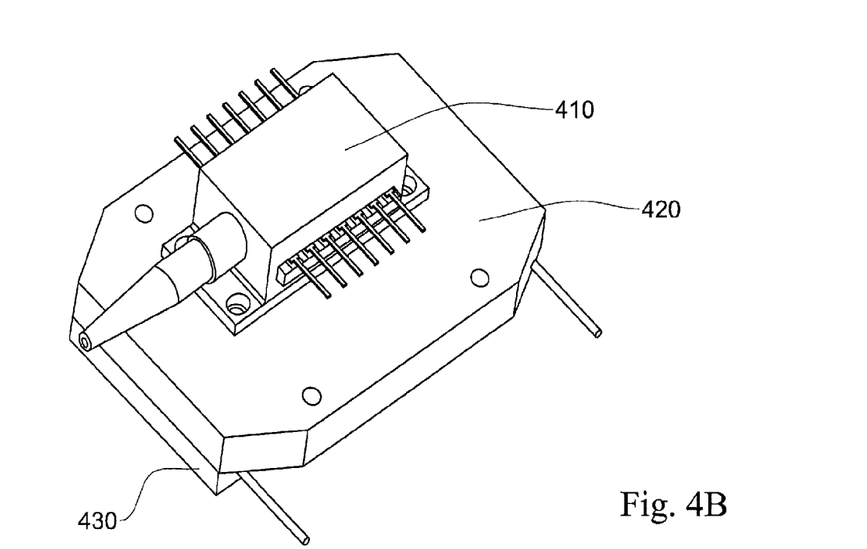
FIG. 4B is a pictorial illustration of the entire system.
Figure 4C:
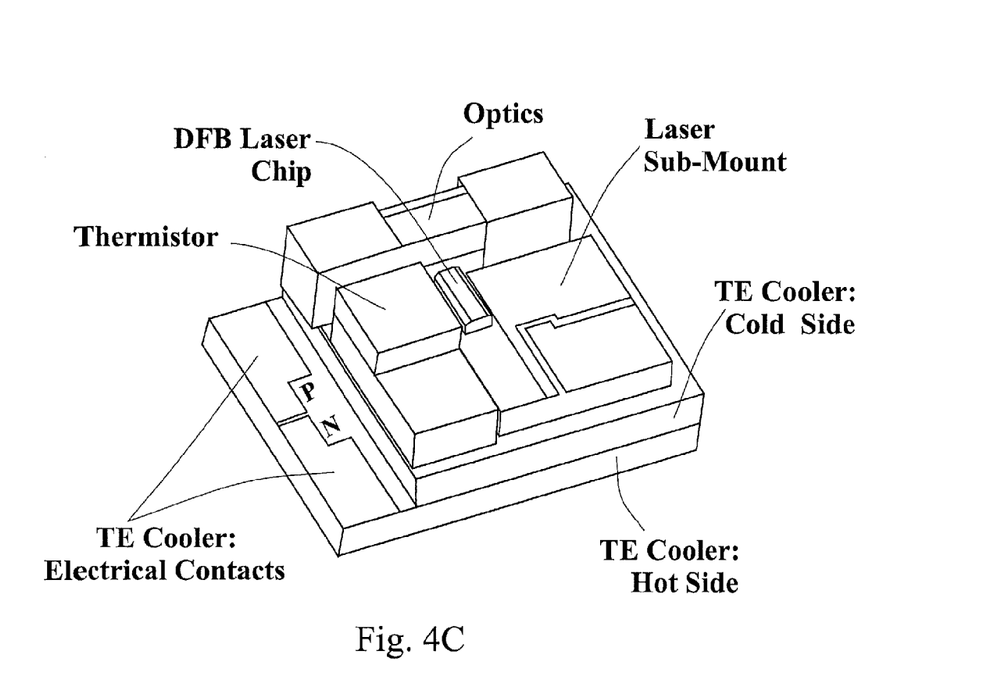
FIG. 4C shows more specifically an assembly of the elements of the system.

In these figures, TEC system 430 of the present invention is implemented as a sub-mount for DFB laser package 410. The TEC system 430 includes a control unit 450, a first heat pumping assembly 431 including a single thin-film thermo-electric heat pump 435, and a second heat pumping assembly 431' including a thermo-electric heat pump 435'. The thin-film thermo-electric heat pump 435 is mounted either directly on the DFB laser package 410 or optionally coupled to the DFB laser through a heat spreader 420 which spreads the heat produced in the laser before it reaches the heat pump 435. The thin-film thermo-electric heat pump 435 has a heat pump rate of about 600 mW/mm$^2$ and is capable of sweeping the DFB laser in a range of about 5° C. to 45° C.

Hence, conversely to the known cooling techniques, the first heat pumping assembly 431 (e.g. thin-film heat pump 435) is operated with a temperature below the nominal operational temperature of the DFB laser, e.g. most of the time at negative temperature difference ΔT between the temperature $T_I$ of its heat drain side (which is kept at temperature of ~10° C.) and the temperature $T_S$ of the heat source side (which varies between 5° C. to 45° C. when the laser is put in operation), therefore achieving higher cooling speed/rate and faster temperature sweeping and according output frequency sweeping.

The thermo-electric heat pump 435' of the second heat pumping assembly 431' thermally interfaces heat pump 435, e.g. it has a thermal conductive connection/coupling with the second heat pumping assembly 431' which might optionally be implemented utilizing a heat sink/spreader 438 or other heat conductive material(s). Heat pump 435' is operated, by the control unit 450, to stabilize the temperature of this interface (e.g. of the heat sink/spreader 438) at a constant temperature of about 10° C. Accordingly, the first pumping assembly (thin-film heat pump 435) operates to control (change/sweep) the temperature of the DFB laser relative to a constant temperature, therefore achieving more accurate control (than sweeping relative to a variable-temperature ambient). Such fine tuning and control over the laser's temperature may be used for both stabilizing the laser at a constant temperature (which gives constant wavelength) and accurately varying the laser's temperature and output wavelengths.

It should be noted that any type of heat pump (preferably thermo-electric and not necessarily thin-film based) can be used as the heat pump(s) of the first pumping assembly. Also, heat pump(s) of the second heat pumping assembly, which typically has/have larger pumping rates than the first assembly, may be of any suitable type such as TE heat pumps (e.g. thin film, cascaded pumps), gas based refrigerators, air cooling system, water cooling systems, etc. Also, an additional heat sink may be placed in contact with the heat drain side of the second heat pumping assembly, and the temperature of such additional heat sink may be further cooled or stabilized to enable further accurate and fast cooling rates.

In many cases, thermally controlled lasers, such as DFB lasers, are used for obtaining THz radiation. In these cases, photo-mixing of light beams of the two DFB lasers of slightly different wavelengths is used to produce the THz radiation. Variation in the wavelength of the THz radiation is obtained by varying the output wavelength of at least one of the lasers (i.e. by varying its temperature). Preferably, however, the output wavelengths of both lasers are changed in opposite directions by cooling one of the DFB lasers while heating the other one. Improving the heating speed of the second laser, can be obtained, in accordance with the invention, by keeping the heat drain side of the second heat pumping assembly 431' at a constant positive temperature difference $\Delta T$, such as 50° C.

Those skilled in the art will readily appreciate that various modifications and changes can be applied to the embodiments of the invention as hereinbefore described without departing from the scope as defined in and by the appended claims.

What is claimed is:

1. A laser system comprising:
at least a first laser source; and
a thermo-electric (TE) system, said TE system being configured and controllably operable for cooling and/or heating of said at least first laser source according to a predetermined temperature sweeping scheme, thereby providing fast sweeping of a frequency output of the laser system, wherein
said TE system comprises at least first thermo-electric cooling (TEC) system associated with said at least first laser source,
said at least first TEC system comprises at least first and second heat pumping assemblies,
each of said at least first and second heat pumping assemblies has a heat source from which heat is pumped and a heat drain through which pumped heat is dissipated, the heat source of the first heat pumping assembly being thermally coupled to the laser source which is to be cooled by evacuating heat therefrom,
said at least first and second heat pumping assemblies are arranged in a cascade relationship having at least one thermal interface between the heat source of the second heat pumping assembly and the heat drain of the first heat pumping assembly, and said second heat pumping assembly is operable according to the temperature sweeping scheme to provide temperature of the heat drain of said first heat pumping assembly either desirably low or by a certain value lower than temperature of the heat source of said first heat pumping assembly; and
a control unit associated at least with said second heat pumping assembly, and configured and operable for operating said second heat pumping assembly to maintain substantially constant temperature of said thermal interface and for generating an operation scheme specifying heat pumping rates and respective durations according to which said first heat pumping assembly is operated in order to accurately adjust the temperature of said at least first laser source.

2. The laser system of claim 1, wherein
the second heat pumping assembly of the TEC system has a substantially larger heat pumping rate than the first heat pumping assembly, such that, when said TEC system is in operation, a negative temperature difference is obtained between the heat drain and the heat source of the first heat pumping assembly.

3. The laser system of claim 1, further comprising:
a second laser source,
said TE system comprising a second TEC system comprising two heat pumping assemblies, each having a heat source from which heat is pumped and a heat drain through which pumped heat is dissipated, the heat pumping assemblies being arranged in a cascade relationship having at least one thermal interface between the heat source of one of the heat pumping assemblies and the heat drain of the other heat pumping assembly, the heat source of said one of the heat pumping assemblies being thermally coupled to the second laser which is to be heated by transferring heat thereto.

4. The laser system of claim 1, further comprising:
a second laser source,
said TE system comprising a second TEC system comprising two heat pumping assemblies, each having a heat source from which heat is pumped and a heat drain through which pumped heat is dissipated, the heat pumping assemblies being arranged in a cascade relationship having at least one thermal interface between the heat source of one of the heat pumping assemblies and the heat drain of the other heat pumping assembly, the heat source of said one of the heat pumping assemblies being thermally coupled to the second laser which is to be heated by transferring heat thereto.

5. The laser system of claim 1, wherein the laser source comprises a Distributed Feedback (DFB) diode lasers system.

6. The laser system of claim 5, wherein said TE system is operable for sweeping a DFB diode laser in a range of about 5 degrees Celsius to 45 degrees Celsius.

7. The laser system of claim 5, wherein said TEC system comprises a control unit configured and operable for controlling operational temperature of the DFB laser diode thereby controlling output frequency of the DFB system.

8. The laser system of claim 5, wherein said output frequency is controlled to be in Terahertz (THz) range.

9. The laser system of claim 5, wherein said control unit is configured and operable to provide fast output frequency modulation over a wide band of THz frequency range.

10. A Terahertz (THz) emission system comprising the laser system of claim 4, said TE system being configured and controllably operable for cooling and/or heating of at least one of the lasers according to the predetermined temperature sweeping scheme, thereby controlling a photo-mixing process to provide the THz frequency output of the emission system.

11. The Terahertz (THz) emission system of claim 10, further comprising a control unit configured for operating either one or both of the first and second TEC systems to provide fast sweeping of the THz output frequency of the THz emission system within a desired frequency range.

12. A Terahertz (THz) emission system comprising the laser system according to claim 5, said TE system being configured and controllably operable for cooling and/or heating of at least one of the DFB diode lasers according to the predetermined temperature sweeping scheme, thereby controlling a photo-mixing process to provide the THz frequency output.

13. The Terahertz (THz) emission system of claim 12, further comprising a control unit configured for operating said TE system to provide fast sweeping of output frequency of said at least one of the DFB diode lasers, thereby providing the THz frequency output of the THz emission system within a desired frequency range.

14. A Terahertz (THz) imaging system comprising the THz emission system of claim 12.

15. A Terahertz (THz) spectroscopy system comprising the THz emission system of claim 12.

* * * * *